United States Patent
Conkle et al.

(10) Patent No.: US 7,229,615 B2
(45) Date of Patent: *Jun. 12, 2007

(54) METHOD FOR THE PURIFICATION, RECOVERY, AND SPORULATION OF CYSTS AND OOCYSTS

(75) Inventors: Harold N. Conkle, Columbus, OH (US); Joseph E. Schultz, Camarillo, CA (US); Scott J. Blonigen, Hilliard, OH (US); Fred H. Weber, Terre Haute, IN (US); David R. Kilanowski, Dublin, OH (US); Bruce Monzyk, Delaware, OH (US); Timothy M. Werner, Traverse City, MI (US); Chad M. Cucksey, Columbus, OH (US); Hamish A. I. McArthur, Mystic, CT (US); Ted L. Tewksbury, Columbus, OH (US)

(73) Assignee: Pfizer, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/248,552

(22) Filed: Oct. 12, 2005

(65) Prior Publication Data

US 2006/0233838 A1 Oct. 19, 2006

Related U.S. Application Data

(63) Continuation of application No. 09/701,760, filed as application No. PCT/US00/04733 on Feb. 25, 2000, now Pat. No. 6,984,378.

(60) Provisional application No. 60/122,160, filed on Feb. 26, 1999.

(51) Int. Cl.
A61K 63/00 (2006.01)
C12N 1/00 (2006.01)
C12N 1/10 (2006.01)

(52) U.S. Cl. ............... 424/93.1; 435/243; 435/258.1; 435/947

(58) Field of Classification Search ............... 424/93.1; 435/243, 258.1, 947
See application file for complete search history.

(56) References Cited

U.S. PATENT DOCUMENTS

| | | | |
|---|---|---|---|
| 3,147,186 A | 9/1964 | Edgar | |
| 3,617,529 A | 11/1971 | Thompson et al. | |
| 3,617,539 A | 11/1971 | Grutsch et al. | |
| 3,827,557 A | 8/1974 | Fischer | |
| 4,040,388 A | 8/1977 | Miller | |
| 4,208,282 A | 6/1980 | Becker | |
| 4,301,148 A | 11/1981 | Shibata et al. | |
| 4,357,320 A | 11/1982 | Apontowell et al. | |
| 4,438,097 A | 3/1984 | Shirley | |
| 4,458,630 A | 7/1984 | Sharma et al. | |
| 4,469,047 A | 9/1984 | Miller | |
| 4,500,638 A | 2/1985 | Apontowell et al. | |
| 4,505,892 A | 3/1985 | Apontowell et al. | |
| 4,544,548 A | 10/1985 | Davis et al. | |
| 4,593,646 A | 6/1986 | Miller et al. | |
| 4,639,372 A | 1/1987 | Murray et al. | |
| 4,650,676 A | 3/1987 | Schenkel et al. | |
| 4,681,063 A | 7/1987 | Hebrank | |
| 4,681,682 A | 7/1987 | White et al. | |
| 4,724,145 A | 2/1988 | Murray et al. | |
| 4,735,801 A | 4/1988 | Stocker | |
| 4,751,079 A | 6/1988 | Burger et al. | |
| 4,790,943 A | 12/1988 | Dunn et al. | |
| 4,808,404 A | 2/1989 | Bhogal | |
| 4,862,731 A | 9/1989 | Davis et al. | |
| 4,863,731 A | 9/1989 | Davis et al. | |
| 4,913,826 A | 4/1990 | Manning et al. | |
| 4,935,007 A | 6/1990 | Bafundo et al. | |
| 5,004,607 A | 4/1991 | Ragland et al. | |
| 5,006,341 A | 4/1991 | Davis et al. | |
| 5,028,421 A | 7/1991 | Fredericksen et al. | |
| 5,045,313 A | 9/1991 | Frenkel et al. | |
| 5,048,313 A | 9/1991 | Frenkel et al. | |
| 5,055,292 A | 10/1991 | McDonald et al. | |
| 5,068,104 A | 11/1991 | Bhogal et al. | |
| 5,106,617 A | 4/1992 | Federicksen et al. | |
| 5,279,960 A | 1/1994 | Anderson et al. | |
| 5,280,042 A | 1/1994 | Lopes | |

(Continued)

FOREIGN PATENT DOCUMENTS

CA 2098773 12/1994

(Continued)

OTHER PUBLICATIONS

Fuller, A.L., et al, "Analysis of coccodian oocyst populations by means of flow cytometry", J. Protozool, vol. 36, No. 2, pp. 143-146, 1989.

(Continued)

Primary Examiner—Rodney P Swartz
(74) Attorney, Agent, or Firm—Myers Bigel Sibley & Sajovec

(57) ABSTRACT

A vaccine for in ovo vaccination against avian coccidiosis produced by a method including obtaining the coccidial oocysts from a fecal suspension, homogenizing the fecal suspension, separating the oocysts from the fecal debris by either salt flotation using sodium sulfate or gas flotation using air, sporulating the oocysts using hydrogen peroxide and air sparging, bleaching the sporulated oocysts, washing the bleached oocysts, concentrating the sterile washed oocysts and combining the concentrates of various species of coccidial oocysts, and producing a vaccine. The method in whole or in part can be applied to other kinds of encysted protozoa to produce vaccines for various types of animals.

22 Claims, 3 Drawing Sheets

U.S. PATENT DOCUMENTS

Figure 1A:
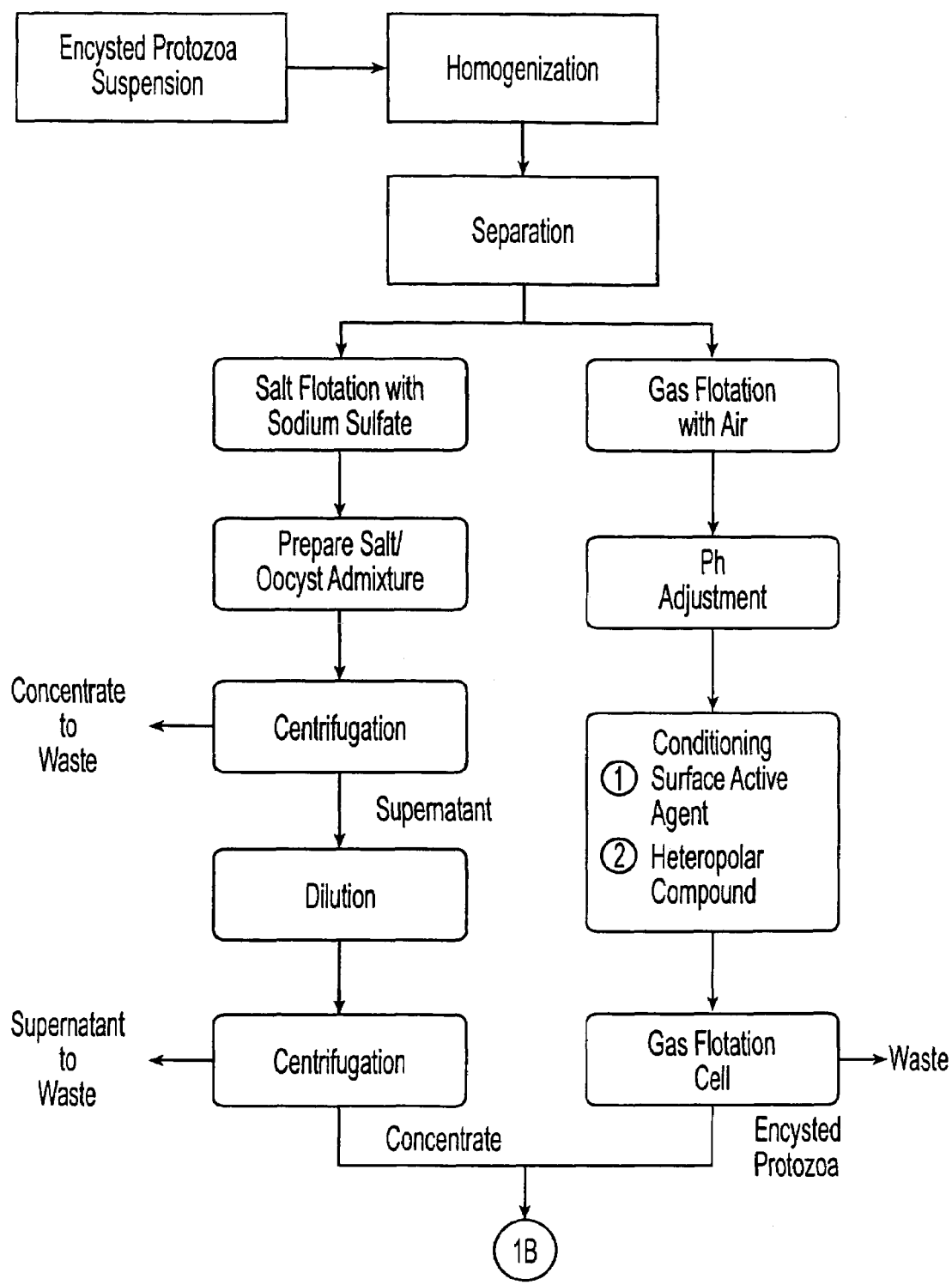
Figure 1B:
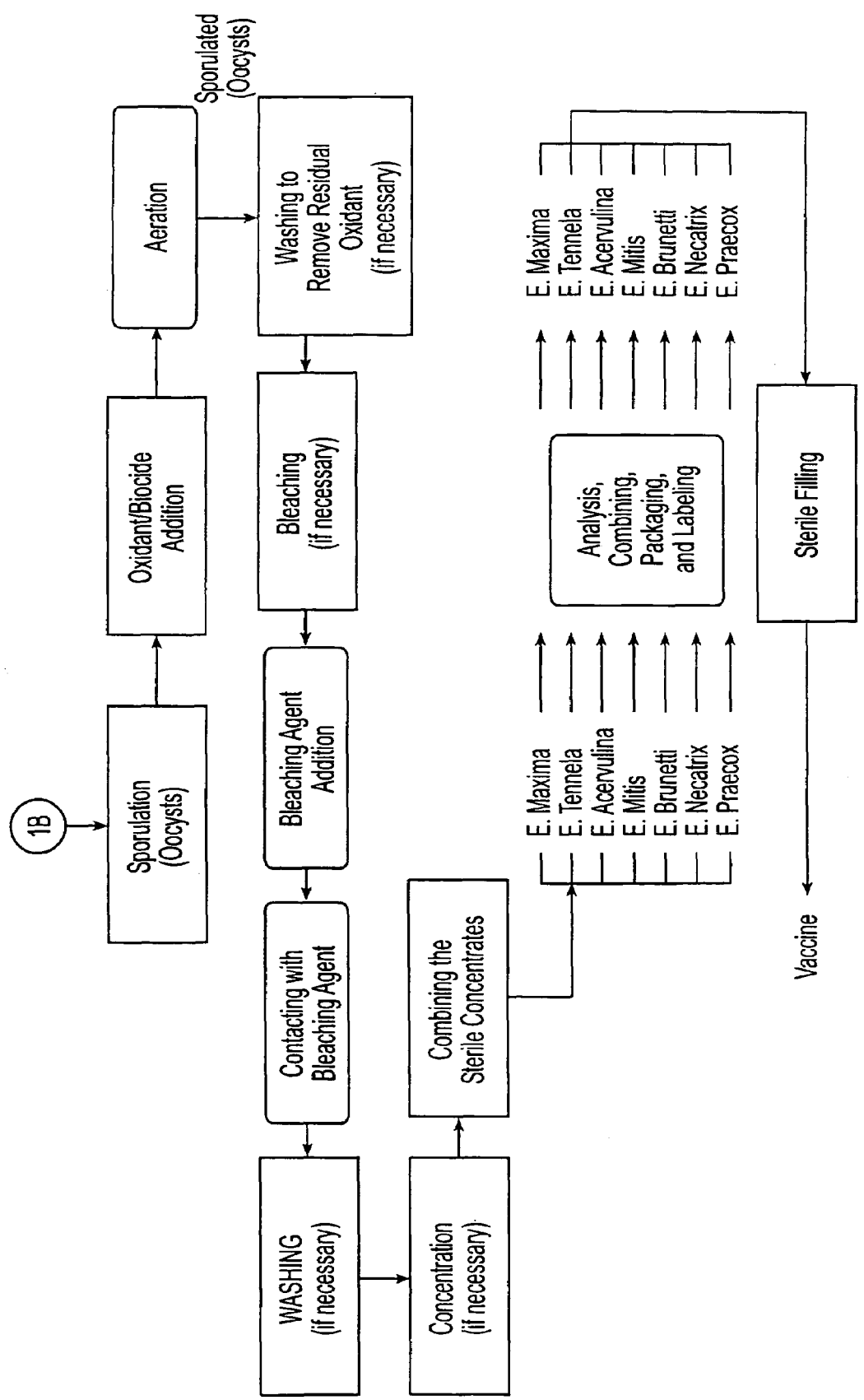

| | | | |
|---|---|---|---|
| 5,288,845 | A | 2/1994 | Chakraborty et al. |
| 5,311,841 | A | 5/1994 | Thaxton |
| 5,339,766 | A | 8/1994 | Phelps et al. |
| 5,359,050 | A | 10/1994 | Chakraborty et al. |
| 5,661,015 | A | 8/1997 | Binger et al. |
| 5,674,484 | A | 10/1997 | Miller et al. |
| 5,702,612 | A | 12/1997 | Wang |
| 5,807,551 | A | 9/1998 | Reynolds |
| 5,843,722 | A | 12/1998 | Bumstead et al. |
| 5,846,527 | A | 12/1998 | Miller et al. |
| 5,932,225 | A | 8/1999 | Wallach et al. |
| 5,997,911 | A | 12/1999 | Brinton et al. |
| 6,019,985 | A | 2/2000 | Brown et al. |
| 6,036,950 | A | 3/2000 | Baker |
| 6,106,854 | A | 8/2000 | Belfer et al. |
| 6,231,871 | B1 | 5/2001 | Coloe |
| 6,306,385 | B1 | 10/2001 | Lee |
| 6,495,146 | B1 | 12/2002 | Evans et al. |
| 2002/0031530 | A1 | 3/2002 | Evans et al. |
| 2002/0090378 | A1 | 7/2002 | Evans et al. |
| 2002/0146435 | A1 | 10/2002 | Evans et al. |

FOREIGN PATENT DOCUMENTS

| | | |
|---|---|---|
| EP | 047662 | 12/1987 |
| EP | 0 256 878 | 2/1988 |
| EP | 256878 | 2/1988 |
| EP | 258045 | 3/1988 |
| EP | 291173 | 11/1988 |
| EP | 0 337 589 | 1/1989 |
| EP | 0 325 359 | 7/1989 |
| EP | 344808 | 12/1989 |
| EP | 109942 | 3/1991 |
| EP | 439056 | 7/1991 |
| EP | 522482 | 1/1993 |
| EP | 650733 | 5/1995 |
| JP | 0828817 | 10/1996 |
| JP | H08-268817 | 10/1996 |
| NL | 8802399 | 4/1990 |
| RU | 2019189 | 9/1994 |
| RU | 2094121 | 10/1997 |
| RU | 2095409 C1 | 11/1997 |
| WO | WO 9301276 | 1/1993 |
| WO | WO 9416725 | 8/1994 |
| WO | WO 96/40233 | 12/1996 |
| WO | WO 96/40234 | 12/1996 |
| WO | WO 9712582 | 4/1997 |
| WO | WO 9814212 | 4/1998 |
| WO | WO 8808699 | 11/1998 |
| WO | WO 00/50072 | 8/2000 |
| WO | WO 01/34187 | 5/2001 |
| WO | WO 02/37961 | 5/2002 |

OTHER PUBLICATIONS

O'Grady, M.R. et al, "An investigation of variables in a fecal flotation technique", Can. J. Comp. Med., vol. 44, pp. 148-154, Apr. 1980.

J.F. Ryley, et al., *Parasitology*, 73, pp. 311-326, 1976.

Smith P.H., et al. "Froth Flotation For Harvesting Chlorella Algae"; Northwest Science, vol. 42, No. 4, 1968, pp. 165-171.

Bare et al., "Algae removal using dissolved air flotation," *Journal WPCF* 47(1): 153-169 (1975).

Bass, "Uncinariasis in Mississippi," *J. Amer. med. Ass.* 47: 185-187 1906).

Davis, "Techniques" 411-458.

Dulski et al, "The Purification of Sporocysts and Sporozoites from Eimeria tennella Oocysts Using Percoll Density Gradients," *Avian Diseases* 32: 235-239 (1988).

Eckert et al., Editors, "Guidelines on techniques in coccidiosis research," *European Commission* 1-24 (1995).

Graat et al., "Rate and course of sporulation of oocysts of *Eimeria vulina* under different environmental conditions," *Parasitology* 108: 497-502 (1994).

Grunnet et al, "Elimination of Ascaris Suum Eggs from Sewage by Air Flotation," *Nord. Vet.-Med.* 29: 458-459 (1977).

Hammond et al., "An improved method for sporulating oocysts in bovine faecal material," *Amer. J. Vet. Res.* 5: 70-71 (1944).

Hill et al., "A mechanical apparatus for screening worm eggs from faeces," *J. Parasit.* 47: 357-362 (1961).

Jackson, "The isolation of viable coccidial sporozoites," *Parasitology* 54: 87-93 (1964).

Jeston et al., "Comparison of the Infectivity of *Eimeria Tenella* Oocysts Maintained at 4, 12 or 28° C Over Time to Determine the Optimal Storage Temperature," *VIIIth International Coccidiosis Conference* (Jul. 2001).

Lane, "The Mass Diagnosis of Ankylostome Infestation (Part I)," *Trans. Roy. Soc. Trop. Med. Hyg.* 16: 274-313 (1923).

Lotze et al., "A practical method for culturing coccidial oocysts in tap water," *J. Parasit.* 47: 5880590 (1961).

Marquardt et al, "The Effect of Physical and Chemical Agents on the Oocyst of *Eimeria zurnii*(Protozoa, Coccidia)," *J. Protozool*7(2): 186-189 (1960).

Marquardt, "Separation of Nematode Eggs from Fecal Debris by Gradient Centrifugation," *The Journal of Parasitology*248-250.

Nyberg et al., "Effect of Sodium Hypochlorite on the Oocyst Wall of *Eimeria tenella*as Shown by Electron Microscopy," *Proceedings of the Helminthological Society of Washington*37(1): 32-36 (1970).

Patnaik, "A Technique of Obtaining Oocysts of Coccidia in Pure State from Chicken Faeces by Modified Marquardt's Method," *The Indian Veterinary Journal* 414-422.

Peterson et al., "Replacement of the Medium for a Natural Phytoplankton Community by Tangential-Flow Filtration, with Special Emphasis on Toxicity Tests," *Bull. Environ. Contam. Toxicol.* 57: 603-609 (1996).

Schmatz et al., "Purification of *Eimeria* Sporozoites by DE-52 Anion Exchange Chromatography," *J. Protozool* 31(1): 181-183 1984).

Smith et al., "Froth Flotation for Harvesting Chlorella Algae," *Northwest Science* 42(4): 165-171 (1968).

Vetterling, "Continuous-flow Differential Density Flotation of Coccidial Oocysts and a Comparison with Other Methods," *The Journal of Parasitology* 55(2): 412-417 (1969).

Whitlock, "The recovery and identification of the first-stage larvae of sheep nematodes," *Aust. vet. J.* 35: 310-316 (1959).

Wilson et al., "Biochemistry of Sproulation in Oocysts of *Eimeria acervulina,*" *Biochemistry of Sporulation* 8(4): 410-416 (1961).

"A Cleaning Method for Coccidial Oocysts Using Density-Gradient Sedimentation," *The Journal of Parasitology*49(1): 159-160.

*International Search Report*, PCT/US02/27668: (Date of Mailing: Jan. 13, 2003).

Kotel'Nikov, G.A., "Diagnosis of Animal Helminthoses," *Moscow Kolos* 1-8, (1974). (English ranslation and Russian language document).

Chervjakov et al., "Handbook, Veterinary Drugs," Moscow, Kolos. (1977) pp. 391-392. (With English Translation).

Ahmad, J. et al. Evaluation of a Modified-Live Virus Vaccine Administered in Ovo to Protect Chickens Against Newcastle Disease, *Am. J. Vet. Res.* 153(11): 1999-2001 (1992).

Hosek, et al., *Improved Method for High-Yield Exystation and Purification of Infective Sporozoites of Eimeria SPP.* J. Protozool 35(4), 1988, 583-589.

Olson, *In Situ Enzyme-Linked Immunosorbent Assay to Quantitate in Vitro Development of Eimeria Tenella* Antimicrob. Agents Chemother 34(7), Jul. 1990, 1435-39.

Perkins, Microscopic Anatomy of Invertebrates vol. 1: Protozoa, Chap. 4: "Sporozoa" 261-331, 1991, Wiley-Liss.

Jeffers, et al., *Embryonic Response to Eimeria Tenella Infection* J. Parisitol., 56(4), 1970, 656-662.

Fredericksen, et al., *In Ovo Administration of a Potential Recombinant Coccidial Antigen Vaccine in Poultry* Les Colloques de L'Inra, 49, 1989, 655-660.

Proceedings of the VI$_{th}$ International Coccidosis Conference, Jun. 21-25, 1993, Guelph, Ontario, Canada, Univ. of Guelph; p. 103, Vaccine Symposium Papers.

Sharma & Burmester, *Resistance to Marek's Disease at Hatching in Chickens Vaccinated as Embryos With Turkey Herpesvirus* Avian Diseases, 26(1), 134-148.

Stedman's Medical Dictionary, 25$^{th}$ Ed., 1990, p. 947, 1087, 1457 and 1458.

Ruff, et al., Poultry Science, 1988, 67 (Supplement I):147.

Shirley; Live Vaccines for the Control of Coccidiosis; Vith International Coccidiosis Conference, p. 61-72 (1993).

Shirley; Development of a live Attenuated Vaccine Against Coccidiosis of Poultry; Parasite Immunology; p. 117-124 (1989).

Watkins, et al.; The Effect of in Ovo Oocyst or Sporocyst Inoculation on Subsequent Coccidial Challenge; VLTH. International Coccidiosis Conference Abstract EL-2, Ontario, Canada (1993). Poultry Science 1597-1602 (1995).

R. B. Williams; The Development, Efficacy and Epidemiological Aspects of Paracox™, A New Coccidiosis Vaccine for Chickens; Mallinckrodt Veterinary LTD.; pp. 1-16 (1992).

Your Questions Answered; Live Attenuated Oral Coccidiosis Vaccine; Paracox, Cocci Vac® Vaccines, Cocci Vac®-T,Cocivac® -D, Cocci Vac® -B, Bursa-Vac®, Bursa-Vac® -3 and Bursa-Vac® -4; Mallinckrodt Veterinary.

The Headlines of the 80'S . . . Immucox; Coccivac Brand of Coccidiosis Vaccines; Mallinkrodt Veterinary; pp. 1-11.

Immucox Coccidiosis Vaccine the Natural Solution; AAP Tek Ingredients, A Divisional of Ontario Limited; pp. 1-6.

M. W. Shirley, et al.; Live Attenuated Vaccines Against Avia Coccidiosis; Parasitology Today; vol. 13 No. 12 pp. 481-484 (1997).

US 7,229,615 B2

METHOD FOR THE PURIFICATION, RECOVERY, AND SPORULATION OF CYSTS AND OOCYSTS

This application is a continuation of U.S. application Ser. No. 09/701,760, filed Apr. 19, 2001 (now U.S. Pat. No. 6,984,378), which is the United States national phase (35 U.S.C. § 371) of International Application Serial No. PCT/US00/04733, internationally filed on Feb. 25, 2000, and which claims the benefit of U.S. Provisional Application No. 60/122,160, filed Feb. 26, 1999, the disclosures of which applications are incorporated herein by reference in their entireties.

BACKGROUND OF THE INVENTION

This invention relates generally to methods for the purification, recovery, and sporulation of encysted protozoa for use in the production of vaccines. Protozoa are pathogens known to attack the gastrointestinal tract of the host. In a situation where the host has a weak or suppressed immune system, such as very young, very old, and immuno-compromised hosts, infection may be fatal. Such a loss can translate into an economic loss as well. Protozoa are present in the environment in a relatively stable cyst form, also termed an oocyst when the protozoa is a sporozoa. Upon ingestion into the host, the encysted protozoa responds to the conditions of the gastrointestinal tract and infects the host.

In order to prevent or alleviate the problem of these diseases, non-in-ovo vaccines have been developed. These vaccines typically expose the host to a low level of the protozoa in order to develop immunity in the host without causing disease. Such vaccines include a vaccine against avian coccidiosis caused from any one of a number of species of coccidia (U.S. Pat. No. 5,055,292), a vaccine for cats against toxoplasma (U.S. Pat. No. 5,045,313), and vaccines for pigs and other ruminants (U.S. Pat. No. 4,808,404). These vaccines are only partially effective because they must be given by gavage or applied to the water or the food of the animal. Gavage is ineffective because it requires manual vaccine introduction. Also, many chicks die due to handling. Adding the vaccine to the food or water is also ineffective as young chicks eat little directly after hatching; therefore, disease control is delayed. The result is less rapid weight gain and a longer time to reach market weight.

In order to produce the vaccine, a supply of adequately purified encysted protozoa must be obtained. Current separation and recovery techniques employ corrosive, hazardous, toxic materials. Measures must be undertaken to compensate for these materials such as extensive washing operations to remove these materials which results in low product yield. The typical method of obtaining the encysted protozoa includes obtaining a source of encysted protozoa, such as the intestines or feces of infected animals. The intestinal matter or fecal matter needs to be separated from the encysted protozoa, and a flotation method is used. Heavy media flotation or sedimentation processes have been used where the heavy media is sodium chloride (U.S. Pat. No. 4,863,731) or sucrose (U.S. Pat. No. 5,068,104). The heavy media is used in an aqueous mixture. Unfortunately, the use of aqueous mixtures of the heavy media can have adverse effects. For example, aqueous mixtures of sodium chloride can lead to severe equipment corrosion.

Before the encysted sporozoa can become infective, the separated oocysts must be sporulated by mild oxidation. Mild oxidation is accomplished by either placing the suspension on a shaking table or bubbling air through the suspension of the oocysts. Potassium dichromate is typically employed to suppress any unwanted microbial growth during sporulation. But, potassium dichromate is a hazardous material. Its use creates handling and disposal problems. Its removal results in reduced yield and increased costs.

A final bleaching step using sodium hypochlorite is used to eliminate any remaining organic material and undesired microorganisms. The bleached encysted protozoa must be washed to reduce the residual bleaching agent concentration to an acceptable level. Washing is accomplished by a series of dilutions and oocyst recovery operations to reduce the bleaching agent levels while producing an oocyst concentrate. The final encysted protozoa concentrate is made into a vaccine under sterile conditions. Each vaccine may include multiple species of protozoa to provide the greatest amount of protection possible.

A need exists for a more efficient vaccination method. Such a vaccination method would employ a live vaccine dosed at a level sufficient to generate an immuno-response to build immunity but low enough not to cause acute symptoms. For example, an in-ovo vaccine against avian coccidiosis can shorten treatment times and allow a more uniform dosage. This method could also be used to collect and produce human vaccines for protection against protozoa including *Cryptosporidium* and *Giardia lamblia*. The method would employ a non-corrosive dense media flotation process or a gas flotation process that eliminates the need for salt entirely. This improved method would not use a hazardous biocide such as potassium dichromate. Such an alternative biocide or oxidant could also double as a bleaching agent, eliminating another step in the process and another hazardous compound.

SUMMARY OF THE INVENTION

The present invention is directed to a method for the purification and recovery of encysted protozoa, including separating the encysted protozoa from a suspension containing the encysted protozoa by either a salt flotation process where the salt is salts such as sodium sulfate, magnesium sulfate, magnesium chloride, calcium chloride, or mixtures thereof, or a gas flotation process.

In one embodiment, the method of separating the encysted protozoa is accomplished by a salt flotation process and the salt is sodium sulfate. In this embodiment, the method includes preparing an admixture comprising the encysted protozoa and the sodium sulfate, centrifuging the slurry and recovering a supernatant therefrom, forming a dilution of the supernatant and centrifuging the dilution, and recovering the concentrate from the centrifuged dilution. This embodiment may also include homogenizing the admixture by high intensity homogenization. The sodium sulfate is present in the admixture in an amount from about 3 to about 30 weight percent. Further, the specific gravity of the dilution may be less than the specific gravity of the encysted protozoa. The concentrate comprises from about $1 \times 10^4$ to about $1.5 \times 10^6$ encysted protozoa/ml.

In another embodiment, separation of the encysted protozoa is accomplished by the gas flotation process. The gas flotation process includes adjusting the suspension to a pH sufficient to affect adhesion between bubbles of the gas in the suspension and the encysted protozoa, conditioning the pH adjusted suspension by adding a sufficient amount of a surface active agent compound to selectively coat particles in the suspension and a sufficient amount of a heteropolar compound to produce a stable froth, passing the conditioned suspension through at least one gas flotation cell, and recovering the encysted protozoa from the gas flotation cell. Suitable gases include air. When the gas is air, the pH can be adjusted to about 2.5 to about 3.5. The surface active agent compounds include a sodium salt of long-chain alkyl hydrogen sulfate, a quaternary ammonium compound, a blend of a fatty ammonium acetate and 2-ethylhexanol, an ester/amide compound, an alkyloxy polyethylenoxyethanol, and mixtures thereof. The heteropolar compounds include amyl alcohols, butyl alcohols, terpinols, cresols, and mixtures thereof. Suitable gas flow rates for the gas flotation cell range from about 0.25 to about 1.1 volumes of gas per volume of suspension per minute. In a preferred embodiment, the gas flotation cell comprises at least two serial gas flotation units, and these units can have different gas flow rates.

The present invention is also directed to a method for the sporulation of oocysts which includes forming an aqueous suspension of the oocysts with water and hydrogen peroxide, wherein the hydrogen peroxide is present in an amount sufficient to eliminate unwanted microbiological growth, and aerating the aqueous suspension to sporulate the oocysts. The aqueous suspension may be aerated for a time period greater than about 40 hours under conditions such that the aqueous suspension during aeration has a dissolved oxygen level greater than about 80% of the saturation level at a temperature of about 22° C. to about 32° C. and may have an agitation level sufficient to adequately suspend all the solids. In this embodiment, the aqueous suspension can include an oocyst concentration of about $10^4$ to about $10^6$ oocysts/ml and a hydrogen peroxide concentration of about 1,000 to about 20,000 mg/l.

In a further embodiment, the present invention covers a method for the purification, recovery, and sporulation of oocysts including separating the oocysts from a first suspension comprising the oocysts, and sporulating the separated oocysts by the methods of the present invention. Suitable oocysts are *Eimeria maxima, Eimeria mitis, Eimeria tenella, Eimeria acervulina, Eimeria brunetti, Eimeria necatrix, Eimeria praecox*, and mixtures thereof. In one embodiment, separation of the oocysts is accomplished by a sodium sulfate flotation process which includes preparing an admixture comprising the oocysts and the sodium sulfate, centrifuging the slurry and recovering a supernatant therefrom, forming a dilution of the supernatant and centrifuging the dilution, and recovering the concentrate from the centrifuged dilution.

In another embodiment, separation of the oocysts is accomplished by a gas flotation process which includes adjusting the first suspension to a pH sufficient to affect adhesion between bubbles of the gas in the suspension and the encysted protozoa, conditioning the pH adjusted suspension by adding a sufficient amount of a surface active agent compound to selectively coat particles in the suspension and a sufficient amount of a heteropolar compound to produce a stable froth, passing the conditioned suspension through at least one gas flotation cell, and recovering the encysted protozoa from the gas flotation cell. This embodiment may further include adding a bleaching agent to the sporulated oocysts in an amount sufficient to inactivate residual microorganisms and eliminate residual organic matter, and bleaching the sporulated oocysts. In another embodiment, the bleaching is conducted concurrently with the sporulation, and the bleaching agent is hydrogen peroxide. In yet another embodiment, the bleaching agent is sodium hypochlorite present in an amount from about 5,000 to about 10,000 parts per million free of available chlorine, ozone present in an amount up to about 3% in air, and combinations thereof.

This method may further include washing the bleached oocysts by cross-flow membrane filtration to decrease the residual bleaching agent concentration to an acceptable level. In yet another embodiment, the bleaching agent is sodium hypochlorite present after washing in a concentration sufficient to suppress residual microbial growth, and the bleached and washed oocyst suspension has a concentration from about $1\times10^6$ to about $2.5\times10^6$ oocysts/ml, a maximum solids size of less than about 200 microns, and sodium sulfate present in an amount sufficiently low to not interfere with the viability and infectivity of the cysts or oocysts, preferably less that about 3 percent, more preferably less than about 0.9 percent. This method may further include concentrating the bleached and washed oocysts into a sterile concentrate, combining sterile concentrates of one or more species of oocysts into a combined concentrate, and packaging the combined concentrate under sterile conditions.

BRIEF DESCRIPTION OF THE DRAWINGS

FIG. 1A is a flow chart illustrating embodiments of a first portion method of the present invention;

FIG. 1B is a flow chart illustrating embodiments of a second portion method of the present invention;

FIG. 2 is a plot showing oocyst concentration verses sodium sulfate concentration; and FIG. 3 is a plot showing sporulation percent verses time after cyst harvest.

DETAILED DESCRIPTION OF THE INVENTION

The present method is directed to producing a concentrate of cysts or sporulated oocysts to be utilized in a vaccine. Specifically, the method is directed to producing a concentrate of sporulated avian coccidial oocysts to be used to produce an in-ovo vaccine against coccidiosis. The production of a suitable and acceptable vaccine requires a multi-step treatment process constituting a plurality of unit processes. As shown in FIGS. 1A and 1B, the vaccine production process can include taking a suspension of encysted protozoa, homogenizing the suspension, separating the encysted protozoa from the suspension by either salt flotation or gas flotation, sporulating the encysted protozoa if required, bleaching the sporulated encysted protozoa, washing the bleached product, concentrating the encysted protozoa, combining the concentrates from multiple encysted protozoa, and sterile filling to produce a vaccine. These steps are described in further detail below.

Encysted protozoa, which include cysts and oocysts, may be obtained from various sources including purified suspensions, intestinal linings, and fecal suspensions. Especially when the encysted protozoa are obtained from feces, the suspensions or slurries can include significant amounts of undesirable suspended solids. For example, the suspensions can include from about 1 up to about 20 weight percent solids or feces. Preferably, the suspension includes from about 5 to about 20 weight percent solids when salt flotation is used and about 1 weight percent when gas flotation is used. In order to liberate the cysts from the associated organics in the suspension, the suspension may be subjected to a homogenization step. The suspension may be homogenized for a time period from about greater than 0 to about 5 minutes, preferably 1 minute depending upon the intensity of the homogenization. The homogenization conditions should be sufficiently intense to liberate the cysts and oocysts but gentle enough to prevent their destruction.

The encysted protozoa need to be separated from this first suspension, preferably to achieve at least about 70% encysted protozoa recovery and at least about 80% solids rejection. Typically, this results in an encysted protozoa concentration of about $1\times10^4$ to about $1.5\times10^6$ encysted protozoa/ml. Separation can be achieved by either a salt flotation process or a gas flotation process.

When a salt flotation process is used, an admixture of the unpurified encysted protozoa and the salt is prepared. Suitable salt solutions include dense solutions of water soluble salts including chlorides, sulfates, phosphates, nitrates, and acetates of ammonium, sodium, potassium, calcium, magnesium, and zinc. Suitable highly hydrogen-bonded organics including urea and the salts of guanidiene. Preferably, the salts include sodium sulfate, sodium chloride, magnesium sulfate, magnesium chloride, calcium chloride, and mixtures thereof. More preferably, the salt is sodium sulfate. These salts provide the benefit of being significantly less corrosive to the process equipment. The salt is added in an amount sufficient to produce a difference between the specific gravities of the encysted protozoa and the admixture. Preferably, the specific gravity of the encysted protozoa will be less than the specific gravity of the admixture. The salt is present in an amount from about 3 to about 30 weight percent, preferably about 14 to about 20 weight percent, more preferably about 20 weight percent.

Figure 2:
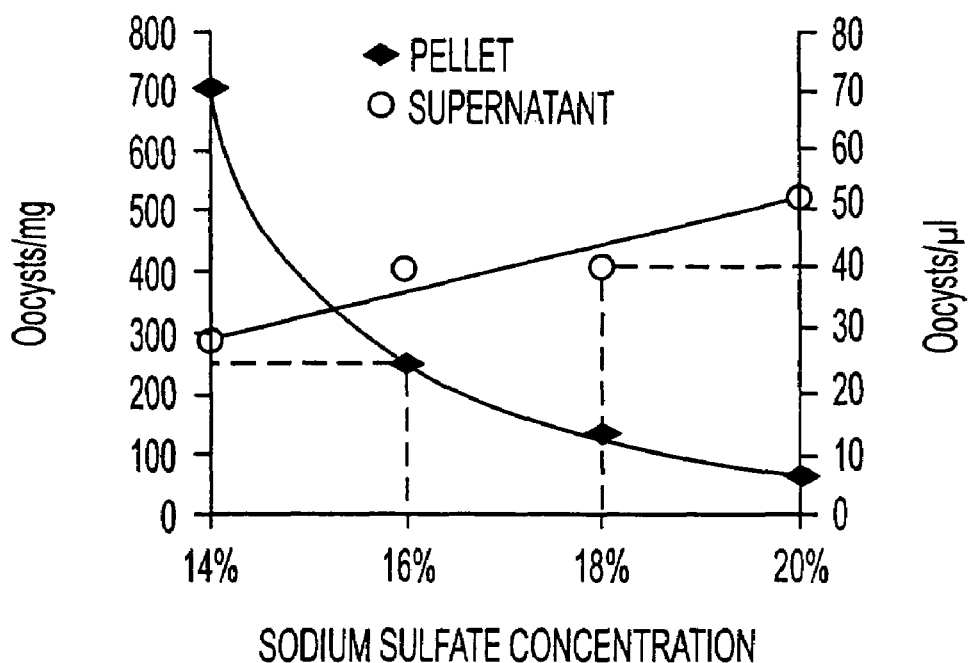

The admixture is then subject to centrifugation and the supernatant and concentrate are collected. Depending upon the admixture conditions, the encysted protozoa can be contained in the supernatant or the concentrate. The admixture is centrifuged at about 3000 to about 15,000 g, preferably 12,000 g for a period of time necessary to adequately separate the encysted protozoa, typically up to about 10 minutes. For a 20% sodium sulfate solution, the encysted protozoa will be contained in the supernatant; therefore, the supernatant is collected and the concentrate or pellet is directed to waste. As shown in FIG. 2, a sodium sulfate concentration of 20% provides for a high concentration of encysted protozoa (oocysts in this case) in the supernatant (product) and only a small amount of encysted protozoa in the pellet (waste). A dilution is formed by the addition of water to the recovered supernatant. The supernatant is diluted sufficiently so that the specific gravity of the encysted protozoa is more than the specific gravity of the dilution. Therefore, the encysted protozoa will tend to settle in the dilution. For a sodium sulfate concentration of 20%, the ratio of the weight of the dilution to the weight of the supernatant is from about 4 to about 8.

The dilution is then centrifuged for a second time under comparable centrifugation conditions as in the first centrifugation, such that the residual salt concentration is less than about 10 weight percent, preferably less than about 1 weight percent, and the resulting cyst concentration is about $10^4$ to $10^6$ cysts/ml representing about 80 to about 95 percent recovery. The solid debris rejection rate is preferably about 90 to about 99 percent. In this embodiment, the encysted protozoa are recovered from the concentrate and the supernatant is directed to waste.

In another embodiment, separation of the encysted protozoa is accomplished by a gas flotation process. Preferably the gas is air, although any gas including oxygen and nitrogen could be used. When gas flotation is used, the pH of the suspension is adjusted to a pH sufficient to affect adhesion between the gas bubbles in the suspension and the encysted protozoa by changing the surface chemistry of the encysted protozoa. The pH is typically adjusted to a pH of about 2 to about 9, preferably about 2.5 to 3.5, more preferably about 3.

The pH adjusted suspension is additionally conditioned by the addition of a surface active agent compound, sometimes referred to as a collector compound and a heteropolar compound, sometimes referred to as a further compound. The surface active agent compound, also termed a selective detergent, wetting agent, or emulsifier, is added in an amount sufficient to promote contact between selected solids and the gas bubbles by forming a thin coating over the particles to be floated, rendering these particles hydrophobic, while not coating other particles. Therefore, through selection of the surface active agent compound, the particles to be floated can be determined. Therefore, the encysted protozoa could be collected in a gas flotation process in which they are floated or in a reverse flotation process in which the solids to be removed are floated. Suitable surface active agents include a sodium salt of long-chain alkyl hydrogen sulfate, a quaternary ammonium compound, a blend of a fatty ammonium acetate and 2-ethylhexanol, an ester/amide compound, an alkyloxy polyethylenoxyethanol, and mixtures thereof. Preferably, the surface active agent compound is sodium lauryl sulfate. The surface active agent should be present in an amount sufficient to coat the particles to be floated. The surface active agent is present in an amount from about 0.5 to 2 lb per ton of solids in the conditioned suspension, preferably 0.5 lb per ton of solids. Alternatively, the surface active agent compound can be about 0.5 lb dodecyl amine per ton of solids which has been acidified with hydrochloric acid until a neutral pH is obtained, or about 0.5 lb potassium salt of oleic acid per ton of solids.

The heteropolar compounds are selected for their ability to change the surface tension of the water and produce stable froths. Typically, these heteropolar compounds contain one or more hydrocarbon groups attached to one polar group, with the hydrocarbon radical having upwards of 5 or 6 carbon atoms. Suitable heteropolar compounds include amyl and butyl alcohols, terpinols, cresols, and mixtures thereof. Preferably, the heteropolar compound is methyl isobutyl carbinol (MIBC) also referred to as methyl amyl alcohol and most accurately referred to as 4-methylpentanol,-2. The heteropolar compound is present in an amount sufficient to produce a stable froth. Preferably, the heteropolar compound is present in an amount up to about 2.0 lb per ton of solids, more preferably from about 0.5 to 2.0 lb per ton of solids, most preferably about 0.5 lb per ton of solids.

The conditioned suspension is passed through a gas flotation cell and the encysted protozoa are recovered. Depending upon the pH, surface active agent compound, and heteropolar compound selected, the encysted protozoa may be floated or retained in suspension. Preferably, the encysted protozoa are floated. The gas flotation process is conducted for a period of time and at an air flow rate sufficient to recover about 20 to 100 percent, typically about 85 percent of the encysted protozoa while rejecting about 20 to 90 percent, typically 70 percent of the solid debris. The gas flotation process is conducted for a period of time of about 3 minutes to greater than about 10 minutes, preferably about 10 minutes. The gas flow rate in the air flotation cell is about 0.25 to about 1.1 volumes of gas per volume of solution per minute ("vvm"), preferably about 0.25 to about 0.83 vvm, more preferably about 0.25 to about 0.75 vvm. The gas flotation cell may include a plurality of serial flotation units. Preferably, the gas flotation cell includes at least two serial flotation units. Preferably, the flotation units are gas flotation columns. The gas flow rate in the serial flotation units may be the same or different. Preferably the gas flows are different, for example about 0.47 vvm for a 32 inch high, 2 inch diameter column and about 0.27 vvm for a 60 inch high, 2 inch diameter column.

Figure 3:
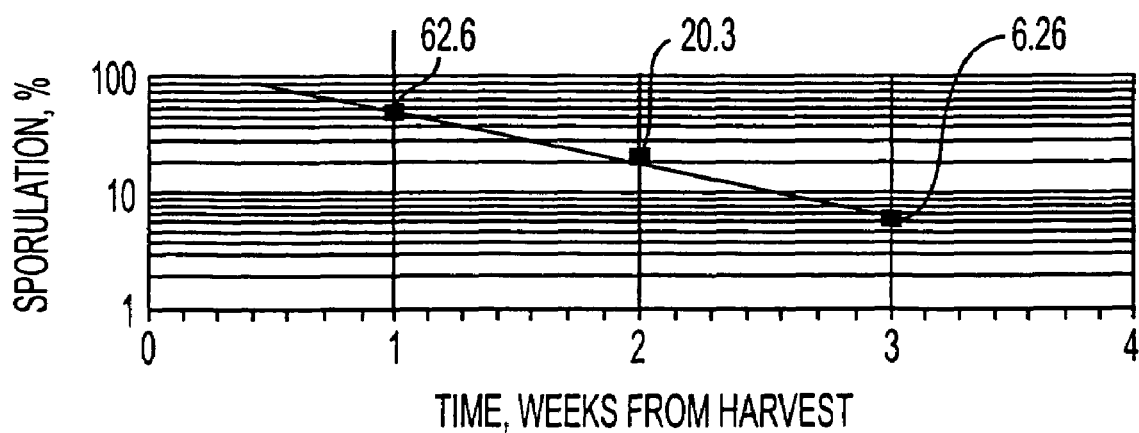

When the encysted protozoa are oocysts or encysted sporozoa, the oocysts are sporulated. As is shown in FIG. 3, sporulation should occur as soon after harvesting the oocysts as possible, preferably, the oocysts should be sporulated within 3 days after harvest. An aqueous suspension of the oocysts and an oxidant or biocide is prepared, and the aqueous suspension is aerated for a period of time sufficient to sporulate the oocysts. If a salt flotation process was used to separate the oocysts, then the salt concentration during sporulation should be less than about 10 weight percent, preferably less than about 2 weight percent, more preferably less than about 1 weight percent. Preferably, the cyst concentration during sporulation is about $10^4$ to about $10^6$ oocysts/ml, more preferably about $10^5$ oocysts/ml. The oocysts should be sporulated within about 1 to 24 hours after recovery of the purified cyst concentrate. The pH of the aqueous suspension should be about 5.0 to 7.0, preferably about 5.2 to 6.8. The temperature of the aqueous suspension in one embodiment is about 20 to about 33° C., preferably about 22 to about 32° C., more preferably about 25 to about 29° C., most preferably about 25° C. The aeration rate in one embodiment is about 0.1 to about 10 vvm, preferably about 0.1 to about 2.0 vvm. Overall, the agitation level should be sufficient to fully suspend all solids during sporulation but not enough to destroy the oocysts. This may occur through aeration, shaking, stirring, and combinations thereof. When stirring is used, for example, the stirring should be sufficient to keep the suspended solids in suspension but not enough to destroy the cysts or oocysts. Suitable stirring in a 6 inch diameter vessel can occur at about 121 to 204 rpm, preferably about 197 to 200 rpm, more preferably about 200 rpm. The dissolved oxygen content should be maintained at a level sufficient to permit the oocysts to sporulate, preferably about 80% of the saturation concentration at the given temperature. The time period for sporulation can be up to about 72 hours, preferably between about 40 and about 72 hours, more preferably about 48 to about 50 hours.

The oxidant is added in a sufficient amount to inactivate the undesirable microbial growth in the aqueous suspension. Suitable oxidants, or biocides, include hydrogen peroxide, ozone, potassium dichromate, chlorine, and combinations thereof. In one embodiment, the oxidant is potassium dichromate and is present in an amount of about 2.5 v/w percent. In a preferred embodiment, the oxidant is hydrogen peroxide present in an amount from about 1,000 to about 20,000 mg/l, preferably about 5,000 mg/l. Hydrogen peroxide provides the benefit of easier and less expensive handling, and the generation of a hazardous waste by-product from this process is alleviated.

Aeration can be accomplished by either shaking on a shaker table or air sparging in a sporulation tank (e.g. fermentation tank). Preferably, aeration is accomplished in an air sparging tank because the mass transfer of air is greater, thus reducing the time for sporulation and the required size of the equipment.

Following sporulation, if necessary, the oocysts may be washed to reduce the residual oxidant concentration to an acceptable level. Hydrogen peroxide provides the benefit of eliminating the need for this step. Washing may be accomplished by serial washings, preferably, washing is accomplished by membrane filtration, more preferably by diafiltration. In the case of membrane filtration, the membrane pore size is selected to allow passage of solutes through the membrane while restricting the passage of the oocysts from one side of the membrane to the other. In one embodiment, washing is conducted with water at a transmembrane pressure of about up to about 30 psi, preferably about 20 to about 25 psi, a crossflow velocity of up to about 10 m/s, preferably about 2 m/s, and a flux through the membrane of up to about 10 l/min/m², preferably about 3 l/min/m².

The oocysts may be bleached to inactivate residual microorganisms and to eliminate residual organic matter. First, a sufficient amount of a bleaching agent is added, and then the oocysts are bleached or contacted with the bleaching agent for a sufficient period of time. The oocysts may be bleached for a period of up to 1.5 hours. Suitable bleaching agents include sodium hypochlorite, hydrogen peroxide, ozone, and mixtures thereof. The bleaching agent can be initially present in an amount of about 2,000 to about 20,000 mg/l, preferably about 8000 to about 10,000 mg/l, more preferably, 8000 mg/l. The bleaching agent should not be present in an amount sufficient to cause corrosion in the process equipment. When hydrogen peroxide is used for sporulation, bleaching and sporulation may be conducted concurrently. Following bleaching, the bleached suspension is washed, if necessary, to reduce the residual oxidant concentration to an acceptable level. When sodium hypochlorite is the bleaching agent, the acceptable level is less than about 1 mg/l. Washing can be accomplished by either serial washing or diafiltration.

The bleached suspension can be concentrated into a sterile concentration having a concentration high enough for efficient and effective handling. For example, the final concentrated encysted protozoa suspension can include a maximum solids size of less than about 200 microns, preferably less than about 25 microns, a salt content of less than about 0.9 percent, a free residual chlorine concentration of less than about 1 mg/l but sufficient to keep residual microbial growth suppressed, and a cyst concentration of about $1\times10^6$ to $2.5\times10^6$ cysts/ml.

When numerous encysted protozoa or different species of one genus of encysted protozoa are to be used in a single vaccine, the sterile concentrates from the different species are combined into a single sterile concentrate. For example, the encysted protozoa can be avian coccidial oocysts including *Eimeria maxima, Eimeria mitis, Eimeria tenella, Eimeria acervulina, Eimeria brunetti, Eimeria necatrix, Eimeria praecox*, and mixtures thereof including multiple strains of each. Finally the combined concentrates are subject to filling and packaging under sterile conditions, and a vaccine is produced.

Although preferred embodiments of the present invention have been described, it is understood that the present method can be used to produce other vaccines for numerous types of animal and for humans. This method could, in fact, be used to immunize humans against typical waterborne protozoa such as *Cryptosporidium* and *Giardia lamblia*. Moreover, even though the entire recovery process is described, unit processes thereof may be used independently or inserted into other recovery, monitoring, or treatment schemes without departing from the scope and spirit of the present invention.

What is claimed is:

1. A method for the sporulation of *Eimeria* oocysts, comprising:
   forming an aqueous suspension of the oocysts with water and hydrogen peroxide, wherein the hydrogen peroxide is present in an amount sufficient to eliminate undesirable non-protozoan microbiological growth; and
   aerating the aqueous suspension to sporulate the oocysts.

2. The method of claim 1, wherein the aqueous suspension is aerated for a time period greater than about 40 hours such that the aqueous suspension during aeration has a dissolved oxygen level greater than about 80% of the saturation level at a temperature of about 22° C. to about 32° C. and with an agitation level sufficient to adequately suspend all the solids.

3. The method of claim 1, wherein the aqueous suspension is incubated for a time period up to about 72 hours.

4. The method of claim 1, wherein the aqueous suspension is incubated for a time period between about 40 and 72 hours.

5. The method of claim 1, wherein the aqueous suspension comprises an oocyst concentration of about $10^4$ to about $10^6$ oocysts/ml and an initial hydrogen peroxide concentration of about 1,000 to about 20,000 mg/l.

6. The method of claim 1, wherein the *Eimeria* oocysts are selected from the group consisting of oocysts from *Eimeria maxima, Eimeria mitis, Eimeria tenella, Eimeria acervulina, Eimeria brunetti, Eimeria necatrix, Eimeria praecox*, and combinations thereof.

7. A method for the purification, recovery and sporulation of *Elmeria* oocysts, comprising: separating the oocysts from a first suspension comprising the oocysts: and sporulating the separated oocysts by the method of claim 1.

8. The method of claim 7 wherein the *Eimeria* oocysts are selected from the group consisting of oocysts from *Eimeria maxima, Eimeria mitis, Eimeria tenella, Eimeria acervulina, Eimeria brunetti, Eimeria necatrix, Eimeria praecox*, and combinations thereof.

9. The method of claim 7, wherein separating the oocysts is accomplished by a salt flotation process.

10. The method of claim 9 wherein the salt flotation process comprises:
preparing an admixture comprising the oocysts and the salt;
centrifuging the slurry and recovering a supernatant therefrom;
forming a dilution of the supernatant and centrifuging the dilution; and
recovering the concentrate from the centrifuged dilution.

11. The method of claim 9, wherein the salt comprises sodium sulfate, potassium sulfate, magnesium sulfate, sodium phosphate, potassium phosphate, magnesium phosphate, sodium acetate, potassium acetate, magnesium acetate, or mixtures thereof.

12. The method of claim 11, wherein the salt comprises magnesium sulfate.

13. The method of claim 11, wherein the salt comprises sodium sulfate.

14. The method of claim 7, wherein separating the oocysts is accomplished by a gas flotation process which comprises:
adjusting the first suspension to a pH sufficient to affect adhesion between bubbles of the gas in the suspension and the encysted protozoa;
conditioning the pH adjusted suspension by adding a sufficient amount of a surface active agent compound to selectively coat particles in the suspension and a sufficient amount of a heteropolar compound to produce a stable froth;
passing the conditioned suspension through at least one gas flotation cell; and
recovering the encysted protozoa from the gas flotation cell.

15. The method of claim 7, further comprising:
adding a bleaching agent to the sporulated or sporulating oocysts in an amount sufficient to inactivate residual microorganisms and eliminate residual organic matter; and
bleaching the sporulated or sporulating oocysts.

16. The method of claim 15, wherein the bleaching agent is hydrogen peroxide.

17. The method of claim 16, wherein the bleaching is conducted concurrently with the sporulation.

18. The method of claim 16, wherein the hydrogen peroxide is initially present in an amount from about 2,000 to about 20,000 mg/l.

19. The method of claim 15, wherein the bleaching agent is sodium hypochlorite present in an amount from about 5,000 to about 10,000 parts per million free available chlorine, ozone present in an amount up to about 3% in air, or combinations thereof.

20. The method of claim 15, further comprising washing the bleached oocysts by cross-flow membrane filtration to decrease the residual bleaching agent concentration to an acceptable level.

21. The method of claim 20, wherein the bleached and washed oocyst suspension has a concentration from about $1 \times 10^6$ to about $2.5 \times 10^6$ oocysts/ml, a maximum solids size of less than about 200 microns, and a salt content of less than about 0.9 percent.

22. The method of claim 21, further comprising:
concentrating the bleached and washed oocysts into a sterile concentrate;
combining sterile concentrates of one or more species of oocysts into a combined concentrate; and
packaging the combined concentrated under sterile conditions.

* * * * *

UNITED STATES PATENT AND TRADEMARK OFFICE
CERTIFICATE OF CORRECTION

PATENT NO. : 7,229,615 B2  Page 1 of 1
APPLICATION NO. : 11/248552
DATED : June 12, 2007
INVENTOR(S) : Conkle et al.

It is certified that error appears in the above-identified patent and that said Letters Patent is hereby corrected as shown below:

In the Claims:

Column 9, Claim 7, Line 21: Please correct "the oocysts: and"
　　　　　　　　　　　　　　　To read -- the oocysts; and --

Signed and Sealed this

Thirtieth Day of October, 2007

JON W. DUDAS
*Director of the United States Patent and Trademark Office*